United States Patent [19]

Baudry et al.

[11] Patent Number: 5,046,613
[45] Date of Patent: Sep. 10, 1991

[54] BOX FOR GATHERING DANGEROUS REFUSE

[75] Inventors: Jean-Paul Baudry, Chamalieres; Joëlle Bourg, Royat, both of France

[73] Assignee: Centre Specialities Pharmaceuticals, Cuernon, France

[21] Appl. No.: 487,943

[22] PCT Filed: Nov. 7, 1988

[86] PCT Pub. No.: PCT/FR88/00543
§ 371 Date: May 4, 1990
§ 102(e) Date: May 4, 1990

[87] PCT Pub. No.: WO89/04182
PCT Pub. Date: May 18, 1989

[30] Foreign Application Priority Data

Nov. 6, 1987 [FR] France ............... 87 15803

[51] Int. Cl.⁵ ............................. B65D 83/10
[52] U.S. Cl. ..................... 206/366; 206/365; 206/370; 220/908; 220/346; 220/348
[58] Field of Search ............ 206/363, 365, 366, 370, 206/438; 220/345, 346, 348, 908

[56] References Cited

U.S. PATENT DOCUMENTS

| | | | |
|---|---|---|---|
| 2,313,428 | 3/1943 | Glenn | 220/348 |
| 2,917,210 | 12/1959 | Libit | |
| 3,240,373 | 3/1966 | Dulle | |
| 3,792,803 | 2/1974 | Kessler | |
| 4,375,849 | 3/1983 | Hanifl | |
| 4,453,648 | 6/1984 | Harris et al. | 220/908 |
| 4,580,688 | 2/1986 | Harris et al. | 206/370 |
| 4,667,821 | 5/1987 | Shillington | 206/366 |
| 4,802,579 | 2/1979 | Hall et al. | 206/366 |
| 4,842,138 | 6/1989 | Sandel et al. | 206/370 |
| 4,867,309 | 9/1989 | Germain | 206/366 |
| 4,874,103 | 10/1989 | Quisenberry et al. | 220/908 |
| 4,892,191 | 1/1990 | Nakamura | 206/366 |
| 4,922,597 | 5/1990 | Ikeda et al. | 206/366 |

FOREIGN PATENT DOCUMENTS

| | | |
|---|---|---|
| 80882 | 6/1983 | European Pat. Off. |
| 3505892 | 9/1986 | Fed. Rep. of Germany |
| 418222 | 2/1967 | Switzerland |

Primary Examiner—David T. Fidei

[57] ABSTRACT

The object of the invention is a box for gathering dangerous products or small objects. The box of the invention is formed of a lid (1) and a receptacle (2); the lid is provided on its upper face with a closure consisting of a slide (4) and a pair of slideways (5) and is of frustopyramidal shape; the lid and the receptacle are provided along their open edge with irreversible locking means which prevent their separation once they have been assembled. Application to gathering refuse, particularly in hospitals.

3 Claims, 2 Drawing Sheets

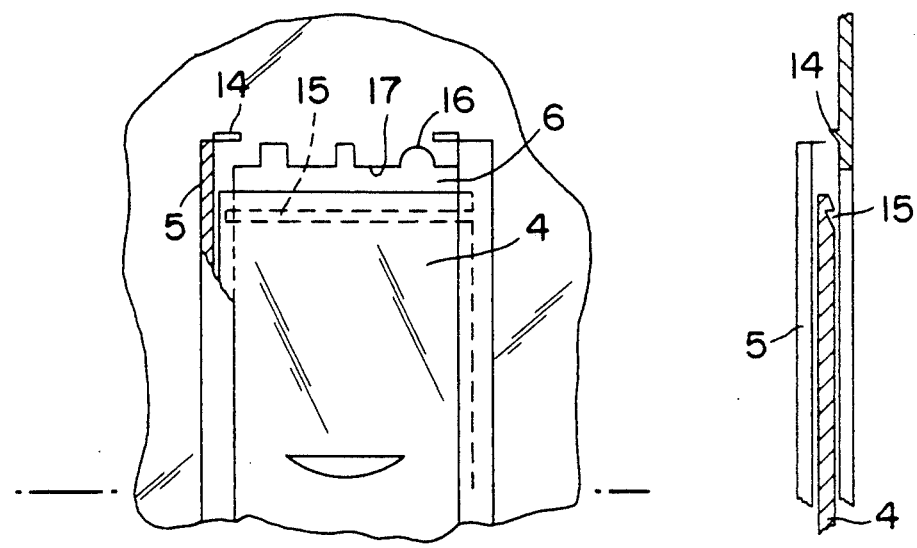
FIG. 5
FIG. 5a
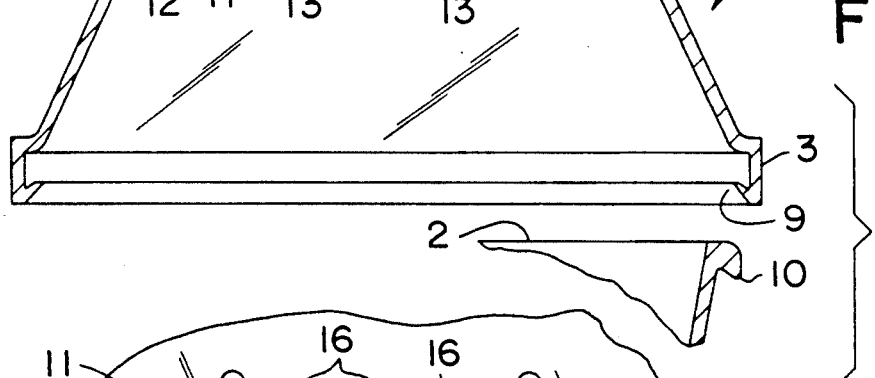
FIG. 4
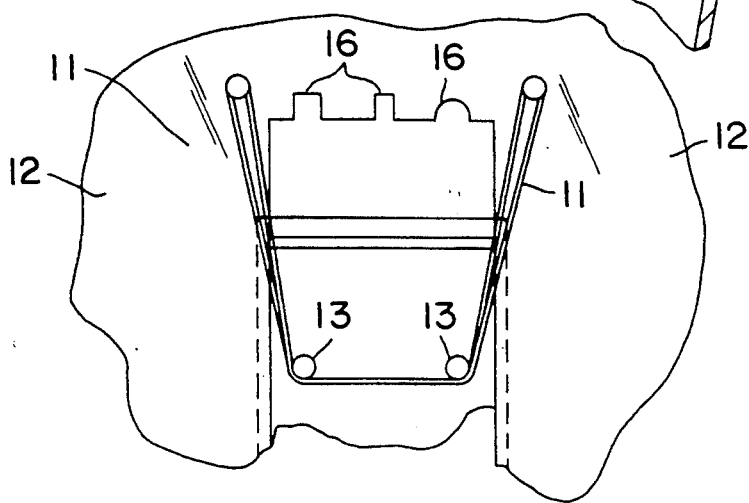
FIG. 6

BOX FOR GATHERING DANGEROUS REFUSE

BACKGROUND OF THE INVENTION

The present invention lies within the field of containers and its object more precisely is a box for the gathering of refuse and small dangerous and discardable objects such as, in particular, small instruments and hospital refuse.

Containers are known for the gathering of miscellaneous refuse such as for instance, used glassware, these containers having means for preventing the removal of the object once it has been placed therein; such containers are generally provided on their upper face with a swivel opening and on their bottom with a slide trap in order to be able to effect the emptying thereof.

From U.S. Pat. No. 3,240,373 a safety closure for bottles is known in which a slide trap is closed after an opening is locked; the edge of the opening is not provided with notches and the locking is not irreversible.

From U.S. Pat. No. 4,375,849 a box is also known which comprises over its lid a rotary part provided with an opening which is intended, by rotation of the cover, to come opposite a hole provided with projections in the lid; the projections of the hole act in the manner of a key to permit the unscrewing of the needle; no irreversible locking means for the lid are provided.

Finally, from U.S. Pat. No. 3,792,803 a bottle closure is known of the same type as in the first patent mentioned, in which the slide is urged into closed position by an elastic means; the edge of the opening has no notches and there are no means to assure the irreversible nature of the closure.

None of said devices is applied for the extraction of attached needles which can be withdrawn by pulling. Now the problems which the present invention is directed at solving are the following: First of all, it is a question of being able irreversibly to close the box when the latter is full of needles in order to bring it to an incinerator, for example; secondly, it is directed at providing the main component elements of this box, namely receptacle and lid, with a conformation which makes it possible for them to be transported and stored in a minimum amount of space.

SUMMARY OF THE INVENTION

More precisely, the object of the present invention is to propose a gathering-box structure which can be used in hospitals, clinics, laboratories, pharmacies and, in general, anywhere that it is desired to conveniently discard, in reliable manner, small objects of refuse such as injection needles, blades, tampons, empty samples or ampules, etc.

In accordance with the present invention, a box for the gathering of dangerous products or small objects is characterized, in particular, by the fact that, being formed of an upper part, referred to as the lid, and of a lower part, referred to as the receptacle, the lid is provided on its upper face with a opening which can be covered over by a closure, and is of frusto-pyramidal or similar shape, which makes it possible to nest several lids one within the other, while the receptacle also is of a frusto-pyramidal shape, which makes it possible to nest several receptacles in each other, the lid and the receptacle being provided along their open edge with irreversible lock means which prevent their separation after they have been assembled.

The closure of the lid is preferably a slide closure formed of a slide and a pair of slideways, the slide being constantly urged into closed position above the opening by an elastic means.

One edge of the opening preferably has three rectangular and/or semi-circular notches intended for the disengagement of the injection needles or the removal of different sections; the lid advantageously comprises, on both sides of the slide, a pair of notches intended to be grasped by one's fingers.

The bottom of the receptacle is preferably curved inwards to form a recess which fits the upper part of the lid and thus confers a certain stability to a stack of boxes.

Preferably, finally, the essential component parts, namely the lid, the receptacle and the closure, are made of plastic material; said plastic material may suitably be a polypropylene.

The present invention will be better understood and details thereof will become evident from the following description of a particular embodiment, read with reference to the accompanying drawing, in which:

BRIEF DESCRIPTION OF THE DRAWINGS

FIG. 4 is a cross-section through the lid along the line A—A;

FIG. 5 is a partial top view of the lid, and FIG. 5a is a corresponding cross-section; and FIG. 6 is a similar view from below.

DESCRIPTION OF THE PREFERRED EMBODIMENTS

Figure 1:
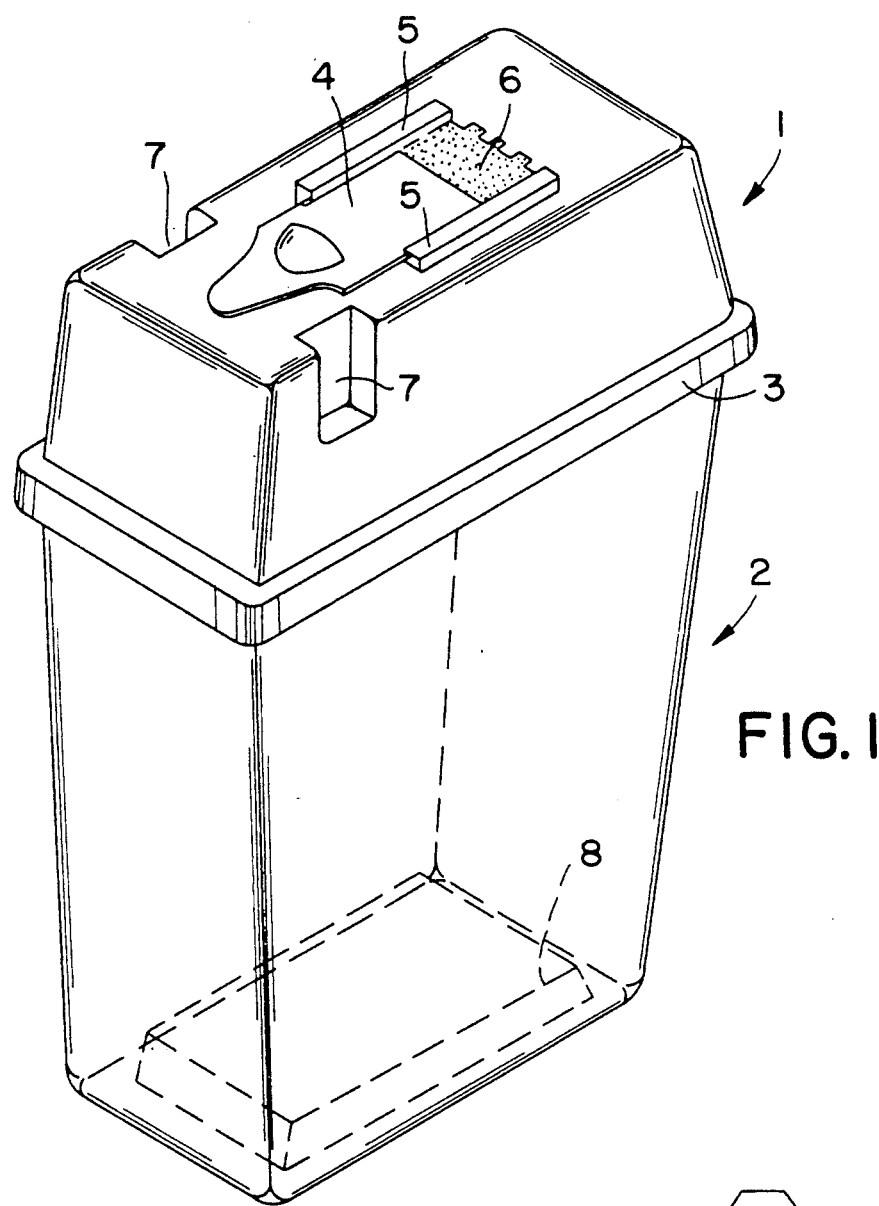
FIG. 1 is a view in perspective of a gathering box in accordance with the invention.

Referring to FIG. 1 a gathering box in accordance with the invention is formed essentially of a lid 1 and a receptacle 2, the lid being placed on the receptacle by means of a rim 3 the functional structure of which will be described further below. The lid as well as the receptacle are of frusto-pyramidal shape, but they could just as well also be of frusto-conical shape or else of a geometrical shape intermediate between these two shapes.

It will be noted from the figure that the lid is provided, on its upper face, with a slide closure formed of a slide 4 which can slide in a pair of slideways 5 so as to close an opening 6 which gives access to the inside of the box; there will furthermore be noted on the lid a pair of notches 7 arranged on opposite sides of the closure, as a result of which the lid can be held firmly between the thumb and the middle finger while the index finger pushes the slide into open position. In another embodiment, not shown in the figures, it is indicated that the slide and its slideways could be arranged under the inner face of the lid, there being evident on the outer face merely a handle which passes through the upper face of the lid.

It will furthermore be noted from this same figure that the bottom of the receptacle is curved inwardly to form a recess 8.

Figure 2:
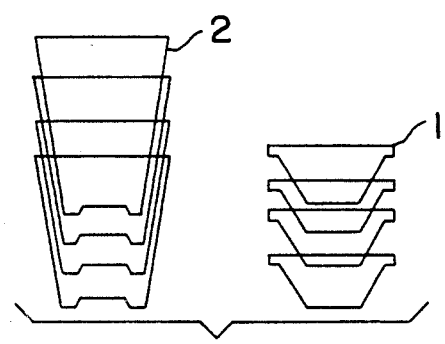
FIG. 2 diagrammatically illustrates the stacking of the two separable parts of the box of FIG. 1.

From FIG. 2 it can be seen how both the receptacles 2 and the lids 1 can be nested in each other in order to take up minimum space upon packing.

Figure 3:
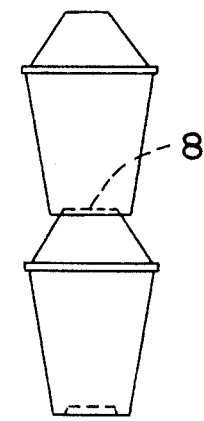
FIG. 3 in similar fashion illustrates the stacking of two boxes.

FIG. 3 shows how, as a result of the recess 8 in the bottom of a box, the box can be placed stably on top of a similar box, which makes it possible suitably to position the boxes in an evacuation package.

From FIG. 4 there will be noted in particular the structure of the edge 3 of the lid 2 which is shaped on the inside with an edge rib 9 which is bent toward the inside; this edge 9 is, in its turn, intended to cooperate with a protruding rim 10 on the receptacle 2; it results from these shapes of the edges of the receptacle and of the lid that a fitting or locking by force of one in the other will be practically irreversible and that the gathering box, once closed, can no longer be opened by mistake.

FIGS. 4 and 6 show a rubber band 11, which serves as means for urging the slide 4 towards its closing position; this band is stretched between two spurs 12 on the lid and two spurs 13 on the slide. Instead of the rubber band, one conceives that the urging or return means could be formed of a steel wire, a so-called piano wire, or else by one or two small spiral springs.

From FIG. 5 more particularly, it appears that the upper face of the cover has, near the ends of the slideways 5, a pair of notches 14 present on the path of the slide 4 and forming a limiter stop for the slide; it is also evident that the end of the slide is provided with a notch 15 on its lower face. When the slide is compelled by strong pressure to pass over the notches 14, the latter will come into engagement in the notch 15, and prevent the opening by simple pressure of the index finger. The gathering box will then be completely closed.

From FIGS. 5 and 6 there can finally be noted rectangular and/or semi-circular notches, such as 16, arranged along a transverse edge 17, of the opening 6. These notches, which can be of different dimensions, are intended to permit the engagement of the tip of the injection needles in order to disengage them from the syringe or bodies of the injection equipment, as a result of which the user does not have to touch the needle itself in order to withdraw it from the syringe.

Although one particular embodiment of the invention has been shown and described, it is to be understood that the scope of the invention is not limited to this embodiment but extends to any recovery box having the general features enunciated above.

What is claimed is:

1. A gathering box for dangerous products or small objects, said box comprising
    a receptacle and a lid which can be irreversibly latched one on the other, the lid having at least one spur and a slide-trap type closable opening which is formed of slide having at least one spur and a pair of slideways, said slide further having means to prevent the box from opening by simple pressure on the slide, wherein the transverse edge of the opening is provided with notches, which notches permit engagement with parts of the dangerous produces or small objects such as the tip of injection needles, and wherein the slide of the slide-trap is constantly urged into the closed position over the opening by a rubber band, which rubber band is stretched between at least one spur located on the lid and one spur located on the slide, and wherein the lid is further provided with a pair of notches on both sides of the slide, which notches facilitate grasping by the user of the gathering box.

2. The gathering box as in claim 1, wherein the receptacle and the lid are provided with latching means which means permit their fitting one on the other by irreversible latching, and wherein the slide-trap type closable opening has means for preventing opening by simple pressure on the slide, which means comprises a pair of projections present in the path of the slide and which projections form a limit-stop for movement, and wherein the edge of the slide has a notch located on its lower face so that when strong pressure is applied to the slide, the projections engage in the notch.

3. The gathering box as in claim 1, wherein the receptacle and the lid are respectively of a frusto-pyramidal shape and a frusto-conical shape, which shape enables them to be fitted respectively one within the other; and
    wherein the base of the receptacle is curved inwardly to form a recess which recess fits the upper part of the lid thereby providing stability when stacking multiple gathering boxes are stacked.

* * * * *